United States Patent
O'Sullivan (10) Patent No.: US 8,355,801 B2
(45) Date of Patent: Jan. 15, 2013

(54) SYSTEM AND METHOD FOR MEASURING ESOPHAGUS PROXIMITY

(75) Inventor: Martin F. O'Sullivan, Long Beach, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 11/236,278

(22) Filed: Sep. 26, 2005

(65) Prior Publication Data

US 2007/0106287 A1    May 10, 2007

(51) Int. Cl.
*A61N 1/00* (2006.01)
(52) U.S. Cl. ......... 607/116; 607/121; 607/122; 607/124
(58) Field of Classification Search ........... 607/121–122
See application file for complete search history.

(56) References Cited

U.S. PATENT DOCUMENTS

| | | |
|---|---|---|
| 4,898,591 A | 2/1990 | Jang et al. |
| 5,037,391 A | 8/1991 | Hammerslag et al. |
| 5,104,393 A | 4/1992 | Isner et al. |
| RE34,502 E | 1/1994 | Webster, Jr. |
| 5,391,199 A | 2/1995 | Ben-Haim |
| 5,427,119 A | 6/1995 | Swartz et al. |
| 5,443,489 A | 8/1995 | Ben-Haim |
| 5,480,422 A | 1/1996 | Ben-Haim |
| 5,487,385 A | 1/1996 | Avitall |
| 5,497,774 A | 3/1996 | Swartz et al. |
| 5,546,951 A | 8/1996 | Ben-Haim |
| 5,558,091 A | 9/1996 | Acker et al. |
| 5,558,665 A | 9/1996 | Kieturakis |
| 5,564,440 A | 10/1996 | Swartz et al. |
| 5,570,671 A | 11/1996 | Hickey |
| 5,575,766 A | 11/1996 | Swartz et al. |
| 5,582,609 A | 12/1996 | Swanson et al. |
| 5,617,854 A | 4/1997 | Munsif |
| 5,674,197 A | 10/1997 | van Muiden et al. |
| 5,681,344 A | 10/1997 | Kelly |
| 5,897,529 A | 4/1999 | Ponzi |

(Continued)

FOREIGN PATENT DOCUMENTS

EP    0 970 718 A2    1/2000
(Continued)

OTHER PUBLICATIONS

Extended European Search Report dated May 18, 2007, issued to European Application No. 07250922.7 (5 pages).

*Primary Examiner* — Nicole F Lavert
(74) *Attorney, Agent, or Firm* — Christie, Parker & Hale, LLP (57) ABSTRACT

A system and method for determining on a continuous, real-time basis the proximity of the esophagus to an endocardial catheter during mapping, ablation or other endocardial catheter-based procedures, comprising an esophagus probe catheter and an endocardial catheter adapted for proximal signal transmission between each other. A signal processing unit is included to process and compare a characteristic of the proximity signal that is changes or attenuates with distance between the two catheters, such as impedance, amplitude and/or phase. Audio and/or optical outputs are provided to alert an operator when the distance between the catheters changes or is below a baseline measurement to avoid damage to the esophagus by the endocardial catheter. The system and method may include adaptations of the catheters with location sensor, and a mapping/navigational system for nonfluoroscopic location determination of the catheters.

18 Claims, 6 Drawing Sheets

U.S. PATENT DOCUMENTS

| | | |
|---|---|---|
| 6,198,974 B1 | 3/2001 | Webster, Jr. |
| 6,285,898 B1 | 9/2001 | Ben-Haim |
| 6,371,955 B1 | 4/2002 | Fuimaono et al. |
| 6,468,260 B1 | 10/2002 | Bumbalough et al. |
| 6,475,214 B1 | 11/2002 | Moaddeb |
| 6,477,396 B1 | 11/2002 | Mest et al. |
| 6,733,499 B2 | 5/2004 | Scheib |
| 7,235,070 B2 | 6/2007 | Vanney |
| 2002/0087089 A1* | 7/2002 | Ben-Haim ............. 600/509 |
| 2003/0045871 A1 | 3/2003 | Jain et al. |
| 2003/0078494 A1* | 4/2003 | Panescu et al. ........ 600/424 |
| 2004/0097801 A1* | 5/2004 | Mesallum ............... 600/407 |
| 2004/0162572 A1 | 8/2004 | Sauer |
| 2004/0193239 A1* | 9/2004 | Falwell et al. ........... 607/122 |
| 2005/0131508 A1* | 6/2005 | Garabedian et al. ..... 607/122 |
| 2005/0143770 A1 | 6/2005 | Carter et al. |
| 2006/0106375 A1* | 5/2006 | Werneth et al. ........... 606/32 |
| 2006/0116576 A1* | 6/2006 | McGee et al. ........... 600/434 |
| 2006/0252993 A1 | 11/2006 | Freed et al. |
| 2007/0118105 A1 | 5/2007 | Miller |

FOREIGN PATENT DOCUMENTS

| | | |
|---|---|---|
| WO | WO 93/20767 | 10/1993 |
| WO | WO 96/26672 | 9/1996 |
| WO | WO 2006/044794 A2 | 4/2006 |
| WO | WO 2006/055286 A2 | 5/2006 |

* cited by examiner

SYSTEM AND METHOD FOR MEASURING ESOPHAGUS PROXIMITY

FIELD OF THE INVENTION

This invention is directed to a system and method for measuring the proximity of the esophagus to the heart, in particular, the proximity of the esophagus to an endocardial catheter in use in the heart.

BACKGROUND OF THE INVENTION

Cardiac arrhythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrhythmias, abnormal regions of cardiac tissue do not follow the synchronous beating cycle associated with normally conductive tissue as in patients with normal sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, such as, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmias, may be of a multiwavelet reentrant type, characterized by multiple asynchronous loops of electrical impulses that are scattered about the atrial chamber and are often self propagating. Alternatively, or in addition to the multiwavelet reentrant type, cardiac arrhythmias may also have a focal origin, such as when an isolated region of tissue in an atrium fires autonomously in a rapid, repetitive fashion.

Several pharmacological approaches intended to remedy or otherwise treat atrial arrhythmias have been disclosed, although such pharmacological solutions are not generally believed to be entirely effective in many cases, and may in some cases result in proarrhythmia and long term inefficacy. Several surgical approaches have also been developed with the intention of treating atrial fibrillation. One particular example is known as the "maze procedure." In general, the maze procedure is designed to relieve atrial arrhythmia by restoring effective atrial systole and sinus node control through a prescribed pattern of incisions about the tissue wall. In the early clinical experiences reported, the maze procedure included surgical incisions in both the right and the left atrial chamber. However, more recent reports predict that the surgical maze procedure may be substantially efficacious when performed only in the left atrium.

Success with surgical interventions through atrial segmentation, particularly with regard to the surgical Maze procedure, has inspired the development of less invasive catheter-based approaches to treat atrial fibrillation through cardiac tissue ablation. Examples of such catheter-based devices and treatment methods have generally targeted atrial segmentation with ablation catheter devices and methods adapted to foim linear or curvilinear lesions in the wall tissue which defines the atrial chambers, such as those disclosed in U.S. Pat. No. 5,617,854 to Munsif, U.S. Pat. No. 4,898,591 to Jang, et al., U.S. Pat. No. 5,487,385 to Avitall, and U.S. Pat. No. 5,582,609 to Swanson, the disclosures of which are incorporated herein by reference. The use of particular guiding sheath designs for use in ablation procedures in both the right and left atrial chambers are disclosed in U.S. Pat. Nos. 5,427,119, 5,497,119, 5,564,440 and 5,575,766 to Swartz et al., the disclosures of which are incorporated herein by reference. In addition, various energy delivery modalities have been disclosed for forming such atrial wall lesions, and include use of microwave, laser and more commonly, radiofrequency energies to create conduction blocks along the cardiac tissue wall, as disclosed in International Publication NO. WO 93/20767 to Stern, et al., U.S. Pat. No. 5,104,393 to Isner, et al. and U.S. Pat. No. 5,575,766 to Swartz, et al., respectively, the disclosures of which are incorporated herein by reference. The use of particular guiding sheath designs for use in ablation procedures in both the right and left atrial chambers are disclosed in U.S. Pat. Nos. 5,427,119, 5,497,119, 5,564,440 and 5,575,766 to Swartz et al., the disclosures of which are incorporated herein by reference. In addition, various energy delivery modalities have been disclosed for forming such atrial wall lesions, and include use of microwave, laser and more commonly, radiofrequency energies to create conduction blocks along the cardiac tissue wall, as disclosed in WO 93/20767 to Stem, et al., U.S. Pat. No. 5,104,393 to Isner, et al. and U.S. Pat. No. 5,575,766 to Swartz, et al., respectively, the disclosures of which are incorporated herein by reference.

The success of catheter based ablation procedures has led to numerous improvements to the catheters used for the procedures. However, the traumatic nature of the ablation procedure has given rise to certain complications. One such complication is the possibility of damaging the esophagus, which lies very close to, and often touches the outer wall of the left atrium. Damage to the esophagus is sometimes caused when the esophagus touches or is close to the tissue in the left atrium that is being ablated. The heat from the ablation procedure may penetrate through the tissue of the left atrium and reach the esophagus. This damage to the esophagus is extremely dangerous, as the damaged esophagus often becomes infected. Due to this infection, an esophageal fistula, or hole in the esophagus, develops over time, causing the infection to spread to the heart wall. This damage to the esophagus carries an extremely high mortality rate.

To avoid damage to the esophagus, a need exists for a method of locating the esophagus during catheter-based procedures within the heart, such as mapping and/or ablation. To that end, some physicians have used standard mapping catheters to record the pre-procedure location of the esophagus. However, such a pre-procedure location determination fails to account for the mobile nature of the esophagus. The esophagus generally does not remain stationary. Rather, the esophagus often moves back and forth thereby positioning itself in different locations relative to the heart wall. As such, the esophagus may change its location during a catheter-based endocardial procedure. The pre-procedure determination fails to account for this movement. Accordingly, a need exists for a method of locating the esophagus during mapping and/or ablation procedures.

SUMMARY OF THE INVENTION

The present invention is directed to a system for continuously monitoring proximity between a catheter in a patient's heart and his esophagus, by placing a second catheter in the patient's esophagus and monitoring the proximity between the two catheters. The system continuously applies proximity interpretation to a measured characteristic of a proximity signal sent between the two catheters and is adapted to provide to the user of the heart catheter an audio and/or visual signal indicative of the proximity and alert when the heart catheter is too close to the esophagus. The system monitors the proximity in real time while the heart catheter is in use in the heart for mapping and/or ablation to minimize the risk of the heart catheter perforating or burning the esophagus.

The system includes an endocardial or heart catheter positioned in a heart of the patient and an esophagus catheter positioned in the esophagus of the patient. A proximity signal is transmitted between the cardiac catheter and the esophagus catheter and a signal processing unit compares signals from the two catheters to determine and monitor the proximity between the two catheters. In one embodiment, where the catheters are separated by a distance, the signal processing unit processes the proximity signal transmitted by one of the catheters and received by the other of the catheters to detect a characteristic of the signal for determining the distance between the catheters. The characteristic can be impedance, signal amplitude or signal phase or other characteristics that change or attenuate with distance. The system continuously monitors the distance so that changes in the distance are monitored on a real-time basis.

In another embodiment, a system for monitoring proximity between a cardiac catheter and an esophagus of a patient, includes a cardiac catheter equipped with a location sensor detecting location signals that are processed by a location processor to determine location of the heart catheter. An esophagus catheter is positioned in the esophagus of the patient at a distance from the cardiac catheter. A proximity signal processor is provided to process the proximity signal transmitted by one catheter and received by the other catheter to detect the distance between the catheters.

The esophagus catheter includes an elongated catheter body having a distal region, and at least one lumen therethrough. In one embodiment, the distal region is adapted to extend in the esophagus generally posterior the left atrium of the patient's heart, and there is at least one electrode or a plurality of electrodes mounted on the distal region adapted for electrical communication of a proximity signal with the heart catheter. The esophagus catheter may also a temperature sensor and/or an electromagnetic location sensor.

The present invention includes a method of measuring proximity between a heart catheter positioned in a patient's heart and the patient's esophagus, by positioning an esophagus catheter in the patient's esophagus, transmitting a proximity signal between esophagus catheter and the heart catheter, and monitoring a characteristic of the proximity signal dependent on or otherwise sensitive to the distance between the catheters.

Nonlimiting examples of suitable analysis techniques for use with the aforementioned system, device and method include impedance measurement, pacing signal amplitude measurement, use of a magnetic field, use of Hall effect sensors, inductance measurement, and capacitance measurement. The present invention allows a physician to continuously monitor, throughout an entire mapping and/or ablation procedure, the position of the esophagus relative to the catheter in use in the heart. This continuous, real time monitoring of the location of the esophagus accounts for the mobility of the esophagus and substantially decreases the risk of damage to the esophagus.

BRIEF DESCRIPTION OF THE DRAWINGS

These and other features and advantages of the present invention will be better understood by reference to the following detailed description when considered in conjunction with the accompanying drawings wherein:

FIG. 3c is a side cross-sectional view of the distal end of the catheter body of the esophageal probe catheter of FIG. 3a.

DETAILED DESCRIPTION OF THE INVENTION

Figure 1:
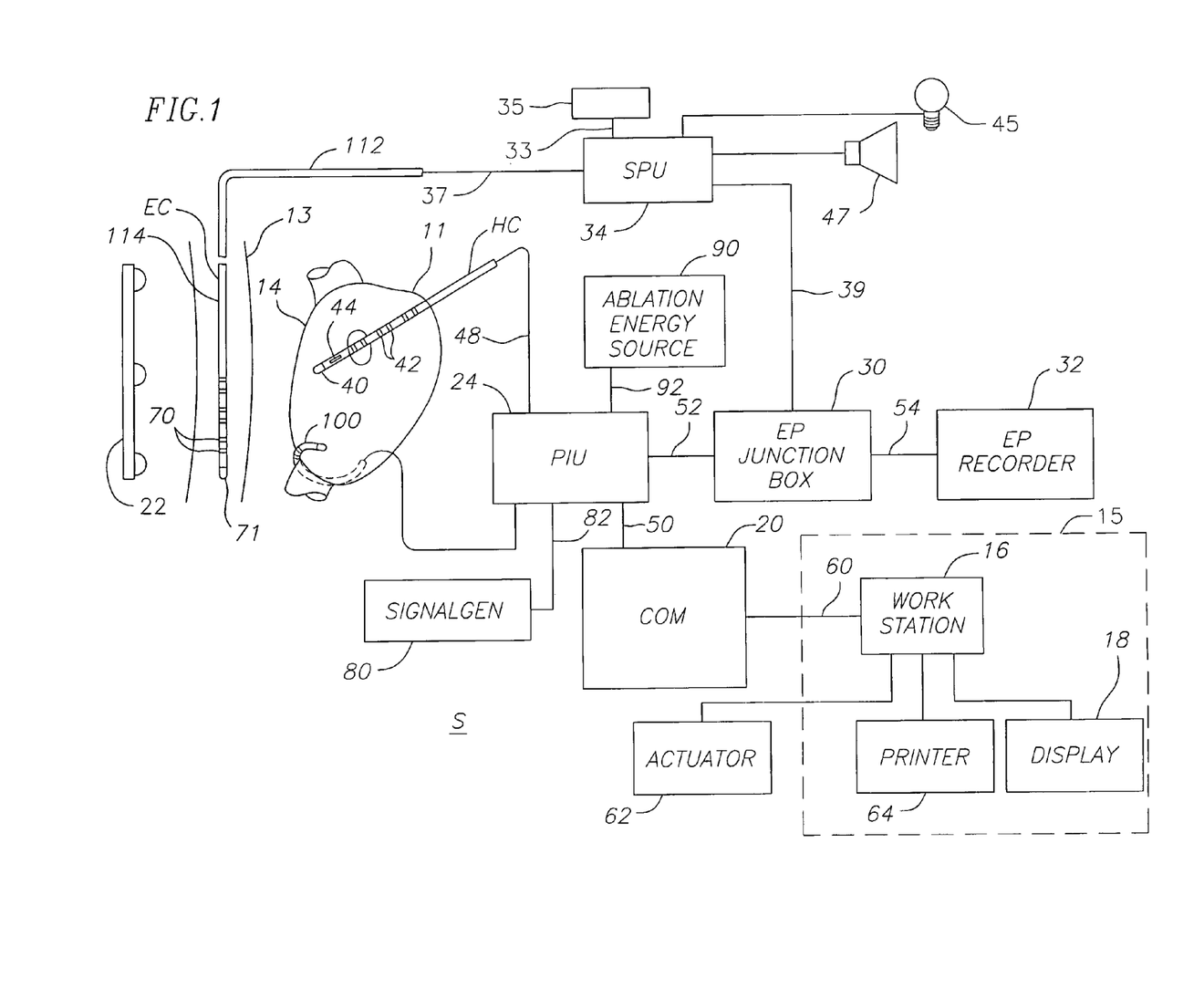
FIG. 1 is a schematic representation of a system according to one embodiment of the present invention.

Referring to FIG. 1, the present invention provides an esophagus proximity measurement system S for continuously monitoring proximity between an endocardial or heart catheter in a patient's heart and his esophagus by detecting and monitoring proximity between the heart catheter and an esophagus catheter in the patient's esophagus. In an embodiment of the system S, as shown in FIG. 1, a heart catheter HC is positioned in the heart, e.g., the left atrium, and an esophagus probe catheter EC is positioned in the esophagus generally posterior of the heart catheter HC. In accordance with the present invention, the system S monitors in real time a separation or distance between the two catheters to provide an indication of their relative position for purposes of monitoring proximity between the heart catheter and the esophagus of the patient so as to avoid the heart catheter coming too close to the esophagus and damaging the esophagus. An audio and/or visual signal representative of the proximity (or changes thereof) is provided to an operator while the heart catheter HC is in the patient and particularly while in use during a procedure such as mapping and/or ablation of left atrium 11. By monitoring the relative position of catheters HC and EC, the operator can minimize, if not avoid, damage to superior wall 13 of the esophagus such as from burn or perforation by the heart catheter HC.

In the disclosed embodiment of FIG. 1, the system S includes a location pad 22 that is placed under the patient, a communication (COM) unit 20 that processes in real time location data of the catheter HC in the patient's heart and electrophysiological data of the heart, such as Local Activation Times (LATs). Coupled to the COM unit 20 is a nonfluoroscopic catheter-based electroanatomical cardiac mapping system 15 that uses the data processed by COM unit 20 to provide simultaneous electrophysiological and spatial information and displays a 3-D reconstruction of the mapped cardiac chamber. The system 15 includes a workstation 16 (with a personal computer storing patient data and maps, a mouse and a keyboard), and a visual display 18 such as an LCD monitor to display the 3-D electroanatomical map.

The system S also includes an electrophysiologic (EP) junction box 30 which processes electrical activity of heart chamber muscle as detected by the catheter HC for recordation and display as electrograms on an electrophysiologic (EP) recorder 32.

The system S further includes a signal processing unit (SPU) 34 to perform proximity interpretation by processing electrical signals that are indicative of the proximity between the two catheters. Electrical signals from both catheters HC and EC are referenced in real time to each other to determine the proximity between the catheters. In the illustrated embodiment of FIG. 1, the SPU 34 has three connectors: a first connector 33 for power supply 35, a second connector 37 for the esophagus catheter EC and a third connector 39 for the heart catheter HC via a patient interface unit PIU which provides cabling connections between most if not all of the components of the system S.

Electrode signals from the heart catheter HC are transmitted to the SPU 34 through the EP junction box 30 which splits the electrode signals between the SPU 34 and the EP Recorder 32. The EP junction box 30 therefore receives electrode signals from both catheters HC and EC and references in real-time one or more selected characteristics of the electrode signals from the catheters that are responsive to changes in the proximity, separation or distance between the catheters HC and EC, as discussed below in further detail.

In accordance with the present invention, a visual and/or audio signal representative of the proximity (or change thereof) between the catheters HC and EC is provided by an optical output 45 and/or an audio output 47. As such, the operator of the heart catheter HC, particularly during ablation and mapping procedures, can assess and be informed on a real-time basis the proximity between the heart catheter HC and the esophagus catheter EC to avoid damage to the superior wall 13 of the esophagus.

Figure 4:
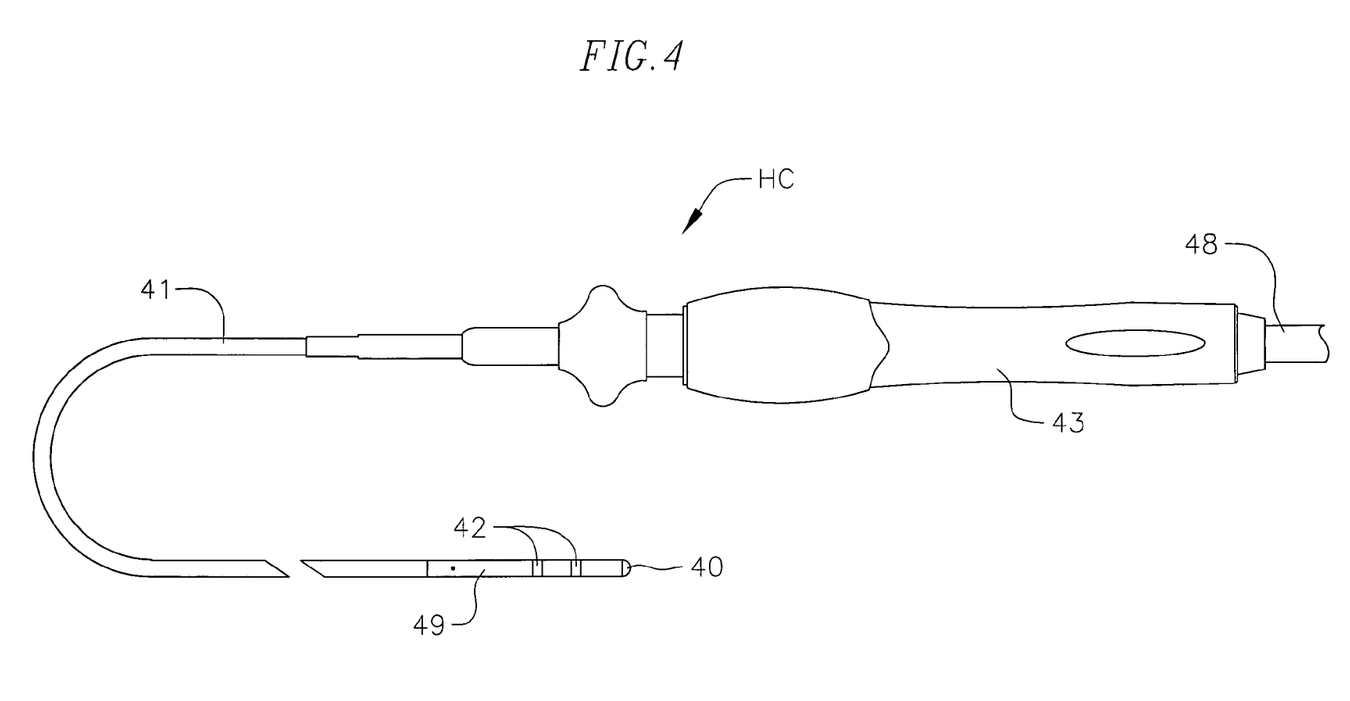
FIG. 4 is a perspective view of an endocardial catheter according to one embodiment of the present invention.

The heart catheter HC may be similar to an electrophysiological deflectable catheter. In one embodiment, as shown in FIG. 4, there is a distal portion 49 that is mounted on a distal end of a catheter body 41 where the distal portion has a tip electrode 40 and several proximal ring electrodes 42 that enable recording of unipolar or bipolar signals representative of electrical activity of the heart chamber muscle, such as of the left atrium 11. In accordance with an embodiment of the present invention, one or more of the electrodes 42 and preferably the tip electrode 40 are also adapted to transmit a proximity signal that travels through a posterior wall 14 of the left atrium 11 and the superior wall 13 of the esophagus to reach the esophagus catheter EC, although it is understood by one of ordinary skill in the art that alternate embodiments may adapt the ring electrodes 42 to also sense proximity signal traveling from the esophagus EC and through the esophagus superior wall 13 and the left atrium posterior wall 14.

Just proximal the tip electrode of the heart catheter HC is a location sensor 44 that is embedded within the catheter which responds to the magnetic fields generated by the location pad 22 to determine location of the heart catheter HC within the patient's heart.

A control handle 43 extends from the proximal end of the catheter body 41. The connector 48 extends between the proximal end of the control handle 43 and the PIU 24 to transmit electrical signals to and from the heart catheter HC.

For mapping a heart chamber, such as the left atrium, and creating an electroanatomical map, the location pad 22 beneath the patient generates external energy fields, for example three magnetic fields, that code a mapping space around the heart chamber with both temporal and spatial distinguishing characteristics. These fields contain information used to resolve the location and orientation of the location sensor 44 in the tip section of the heart catheter HC.

Magnetic field signals received by the location sensor 44 are transmitted through the catheter HC via lead wires to the PIU 24 via the connection 48. The PIU 24 transmits the location signals to the COM unit 20 via connection 50 where the signals are amplified and filtered as appropriate. Data received from the location sensor 44 is processed by the COM unit 20 to obtain location data of the tip of the catheter HC (for example, x, y and z coordinates and also pitch and roll and yaw). Accordingly, a 3-D map of the heart chamber geometry can be generated using a plurality or series of location data obtained by dragging or otherwise moving the distal tip of the heart catheter along the endocardium of the heart chamber.

Local heart electrical activity signals detected by the ring electrodes 42 of the heart catheter HC are transmitted through the catheter HC via separate lead wires to the PIU 24 via the connection 48. From the PIU these signals travel via connection 52 to the EP junction box 30 and to the EP recorder 32 via connection 54. The EP recorder 32 records and displays the electrophysiologic data in the form of an electrocardiograph.

The heart chamber muscle electrical activity detected by the heart catheter are also transmitted to the COM unit 20 which serves as an electrophysiologic signal processor by calculating local activation times (LATs). The LATs are transmitted via connection 60 to the workstation 16 which generates a 3-D real-time electroanatomical map for viewing on the display 18. The map's electrophysiological information may be color coded and superimposed on the 3-D heart chamber geometry generated from the location mapping obtained by the location sensor of the heart catheter described hereinabove. Accordingly, an operator viewing the display is provided with a 3-D graphical representation of the patient's heart that is color coded in regions to show different LATs. For example, the color red represents shorter LATs and the color purple represents longer LATs. In a normal functioning heart, regions closest to the sinus node are red and regions farthest to the sinus node are purple. Using different activation zones in the cardiac chamber, different maps are constructed showing different activation sequences. Thus, in addition to viewing the electrocardiographs provided by the EP recorder 32, the user has access to a 3-D color-coded graphical representation of the patient's LATs.

The system 15 may also include an actuator 62, e.g., a foot pedal, in communication with the system that allows the user to accept or reject data points. The system 15 may also include a printer 64 for printing the color-coded, 3-D graphical anatomical and/or electrophysiological representation of the heart.

For proximity interpretation of the catheters HC and EC, the SPU 34 receives and processes signals detected by electrodes 70 on the esophagus catheter EC and the electrodes 42 on the heart catheter HC. The catheters and the SPU 34 completes a circuit as electrical signals conduct between the two catheters by traveling through the heart tissue, the esophagus tissue and body fluids between the two catheters. Taking into consideration the known electrical properties of such tissue and fluids, the SPU 34 references the electrical signals from both catheters to each other to determine the proximity therebetween.

Where the heart catheter HC is adapted for ablation, an ablation energy source 90 provides energy via connection 92 to the PIU 24 and the connection 48 to the catheter HC. The ablation energy source may be RF in nature, cryogenic, ultrasonic or microwave, as understood by one of ordinary skill in the art.

In one embodiment, proximity interpretation performed by the SPU 34 is based on impedance in the current through the catheters EC and HC, as generated by a signal generator 80 supplying a signal to, for example, the heart catheter HC. The signal, for example, an AC signal of 2 µAmps at 50 kHz, is transmitted to the PIU 24 via connection 82 where the signal is amplified using operational amplifiers and then applied to the tip electrode 40 of the heart catheter HC via the connection 48. The signal flows from the tip electrode 40 of the catheter HC through the posterior wall 14 of the left atrium 11 and the superior wall 13 of the esophagus and any fluids present along this path and is sensed by the electrodes 70 on the catheter EC. Since the current is fixed and flows through a relatively short distance encountering generally consistent tissue and fluid media with little, if any, resistance, change in impedance in the current between the two catheters is primarily attributable to change in the distance between the catheters. Voltages at the electrodes 70 of the esophagus catheter EC and the tip electrode 40 of the heart catheter HC are obtained and amplified by the SPU 34 which includes a microprocessor programmed to take the measured voltages and the respective fixed current outputs and apply Ohm's Law to calculate the impedance. The impedance measured (or a change in the impedance measured) can be displayed on the SPU 34 for reference by the operator.

As the catheters HC and EC approach each other or otherwise come into close proximity of each other, a decrease in intercatheter impedance triggers a visual and/or audio signal to the user via the outputs 45 and/or 47 to caution that the heart catheter distal tip is close to the esophagus. As understood by one of ordinary skill in the art, the audio and/or visual outputs may, for example, be triggered when a threshold proximity has been reached. Or, as another example, the activation frequency of the outputs 45 and 47 may be made proportional to the intercatheter proximity.

In another embodiment, proximity interpretation may also be based on a pacing signal sent by the SPU 34 to the esophagus catheter EC and transmitted by the electrodes 70 to the tip electrode 40 of the heart catheter HC. As the distance between the catheters changes, amplitude of the pacing signal increases. As understood by one of ordinary skill in the art, the activation and/or frequency of activation of the audio/visual signal to the user can be dependent on a change in the amplitude or a threshold amplitude to alert the user that the heart catheter tip is too close to the esophagus. Moreover, in alternative embodiments of the invention, the system S may measure a temporal change in the proximity signal between the two catheter, such as monitoring the phase of the proximity signal, or use inductive sensors (more preferable for metal detection), capacitive sensors, and/or Hall Effect sensors. These sensors may be located in the tip or body of either catheter as appropriate or desired to provide the same function in monitoring on a real-time basis the proximity of the catheters to each other.

In view of the foregoing, it is further understood by one of ordinary skill in the art that the signal for proximity measurement may be transmitted by either one catheter to the other catheter, as the present system detects a characteristic of the proximity signal in monitoring the distance between the two catheters, whether the characteristic is impedance, amplitude or phase.

Under fluoroscopic guidance, or other suitable guidance means, the heart catheter HC is introduced into the patient's body and heart through appropriate vascular access and positioned inside the heart chamber. Additional heart catheters, such as a catheter 100 positioned in the coronary sinus, may be used as a reference catheter or external reference sensors may be used in locating the position of the heart catheter HC. The esophagus catheter EC is also introduced into the patient's esophagus under fluoroscopy.

The catheter HC is dragged over the endocardium, sequentially acquiring the location of its tip together with its electrogram while in stable contact with the endocardium. The system S determines the location and orientation of the heart catheter by means of the COM unit 20 and the system 15. Thus, as the catheter HC is moved inside the heart, the system S analyses its location and presents it to the operator, thus allowing navigation without the use of fluoroscopy.

A local activation time at each site is determined from the intracardiac electrogram as derived from detections by the proximal ring electrodes on the catheter tip. The 3-D chamber geometry is reconstructed in real time by use of the set of location points sampled from the endocardium. On the basis of the various LATs, the map constructed shows the activation sequence resulting from the time activation of different zones in the cardiac chamber. The activation map may be color-coded (e.g., red indicating the earliest and purple the latest activation) and is superimposed on the 3D chamber geometry.

As desired during mapping and/or ablation, proximity signals may be sent by one catheter and received by the other catheter, with the signals being processed by the SPU 34 to provide an audio and/or visual signal to the operator on a real time basis indicating the proximity between the electrode-bearing portion of the heart catheter HC and the electrode-bearing portion of the esophagus catheter EC.

Where the catheter-based procedure includes ablation, a baseline proximity measurement may be taken before ablation begins to represent, for example, a minimum separation or distance to be maintained between the two catheters. To that end, the SPU 34 can be adapted to measure and store a baseline proximity measurement against which subsequent proximity measurements are compared to alert the operator when the catheters are too close to each other. In accordance with the invention, the operator can monitor the distance between the two catheters on a real-time basis and is alerted when the heart catheter HC is too close to the superior wall of the esophagus and can therefore better avoid inadvertently burning the esophagus or perforating it or the wall of the left atrium.

Figure 2:
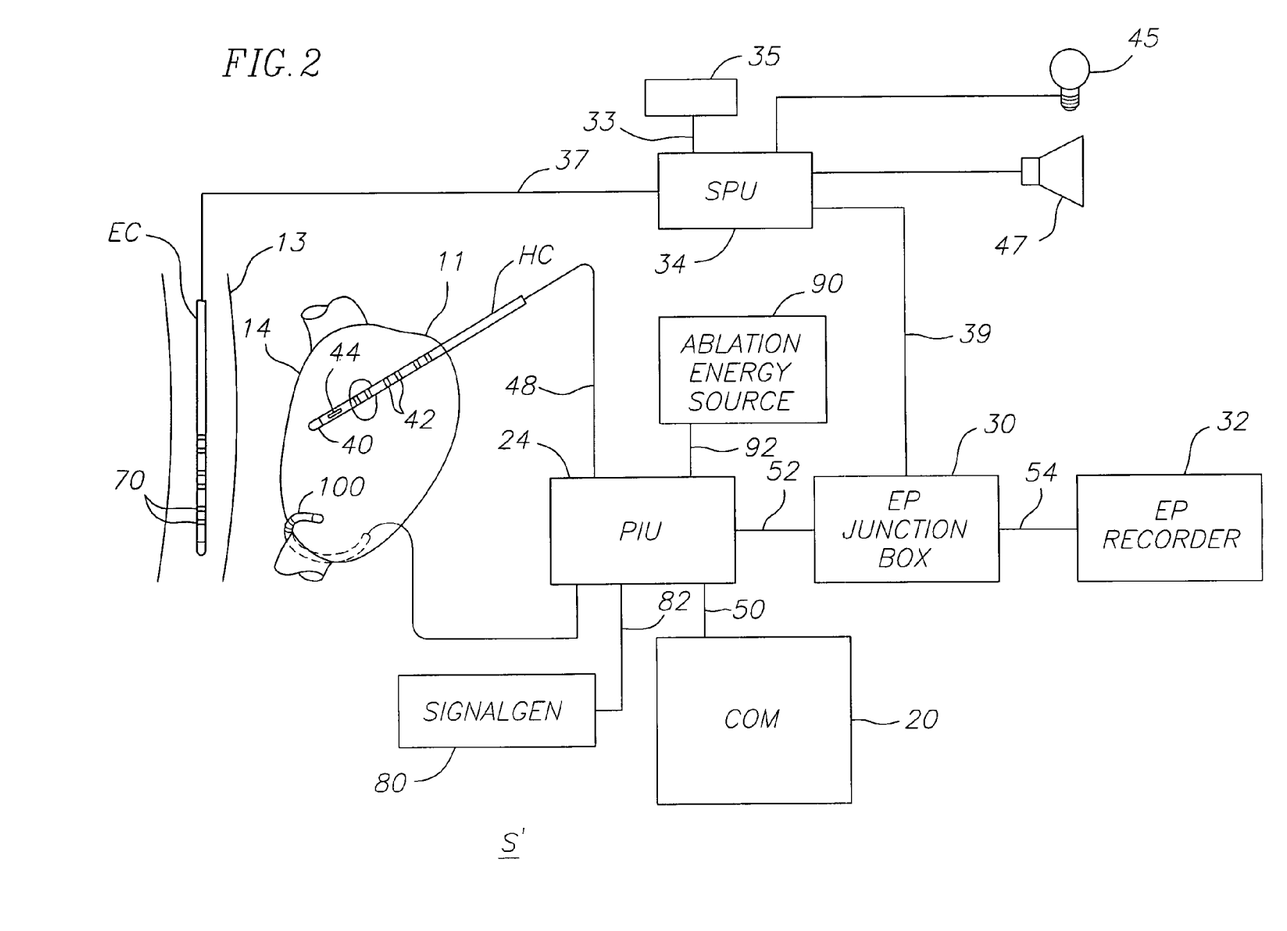
FIG. 2 is a schematic representation of a system according another embodiment of the present invention.

The present invention also contemplates an esophagus proximity detection system S' which can operate without mapping or navigational capabilities, where the heart and esophagus catheters can be introduced into and used in the patient entirely by fluoroscopy as appropriate. As shown in FIG. 2, electrophysiologic data sensed by the electrodes 40 on an endocardial or heart catheter HC are transmitted to the PIU 24, the EP junction box 30 and then the EP recorder 32 where electrograms are stored and/or displayed. Where ablation is to be applied, the ablation energy source 90 is connected to the PIU 24 to energize the tip electrode 40. The esophagus catheter EC is connected to the SPU 34 which completes a circuit with the heart catheter HC via the EP junction box 30 and the PIU 24.

Proximity signals generated by the signal generator 80 are transmitted to the electrode 40 of the heart catheter via the connection 82, the PIU 24 and the connection 48 and are conducted through the heart wall, the esophagus wall and fluids in between, reaching the electrodes 70 of the esophagus catheter EC. In processes similar to those described above, the SPU 34 processes and compares the signals from the catheters HC and EC and sends the appropriate activation signals to the optical and or audio outputs 45 and 47.

It is understood by one of ordinary skill in the art that for the foregoing embodiments, the signals processed and compared by the SPU 34 to determine proximity are preferably those measured at the electrode locations for improved accuracy. Signals obtained or derived from another location (such as directly from the generator 80 in impedance-based proximity measurement or the SPU 34 in amplitude-based proximity measurement) may reflect environmental differences such as different tissues and different fluids that may alter the characteristic measured by the SPU 34.

For the foregoing embodiments, the heart catheter may be similar to an electrophysiological deflectable catheter having a tip electrode and several proximal ring electrodes. The catheter may be adapted for mapping and/or ablation. Nonlimiting examples of suitable ablation catheters for use as the heart catheter HC with tip electrodes and/or ablation assemblies include those described in U.S. Pat. Nos. 6,733,499, 6,477,396, 6,475,214 and 6,371,955, the entire disclosures of which are incorporated herein by reference. Nonlimiting examples of suitable mapping catheters for use as the heart catheter HC are described in a PCT application filed in Israel on Jan. 8, 1997, by applicant "Biosense" and titled "Mapping Catheter", the disclosure of which is incorporated herein by reference.

Moreover, a system 15 for cardiac mapping and navigation may be a CARTO system, available from Biosense (Israel) LTD., Tirat Hacarmel, Israel, for determining the position of a catheter. Suitable electromagnetic sensors for use with the present invention are described, for example, in U.S. Pat. Nos. 5,558,091, 5,443,489, 5,480,422, 5,546,951 and 5,391,199, the entire disclosures of which are incorporated herein by reference The illustrated embodiment of the esophagus catheter EC of FIG. 1, generally comprises an elongated catheter body 112 having proximal and distal ends, and a distal region 114 that is configured to extend into the esophagus. On the distal region, there may be mounted a plurality of electrodes 70 and a distal tip electrode 71.

Figure 3A:
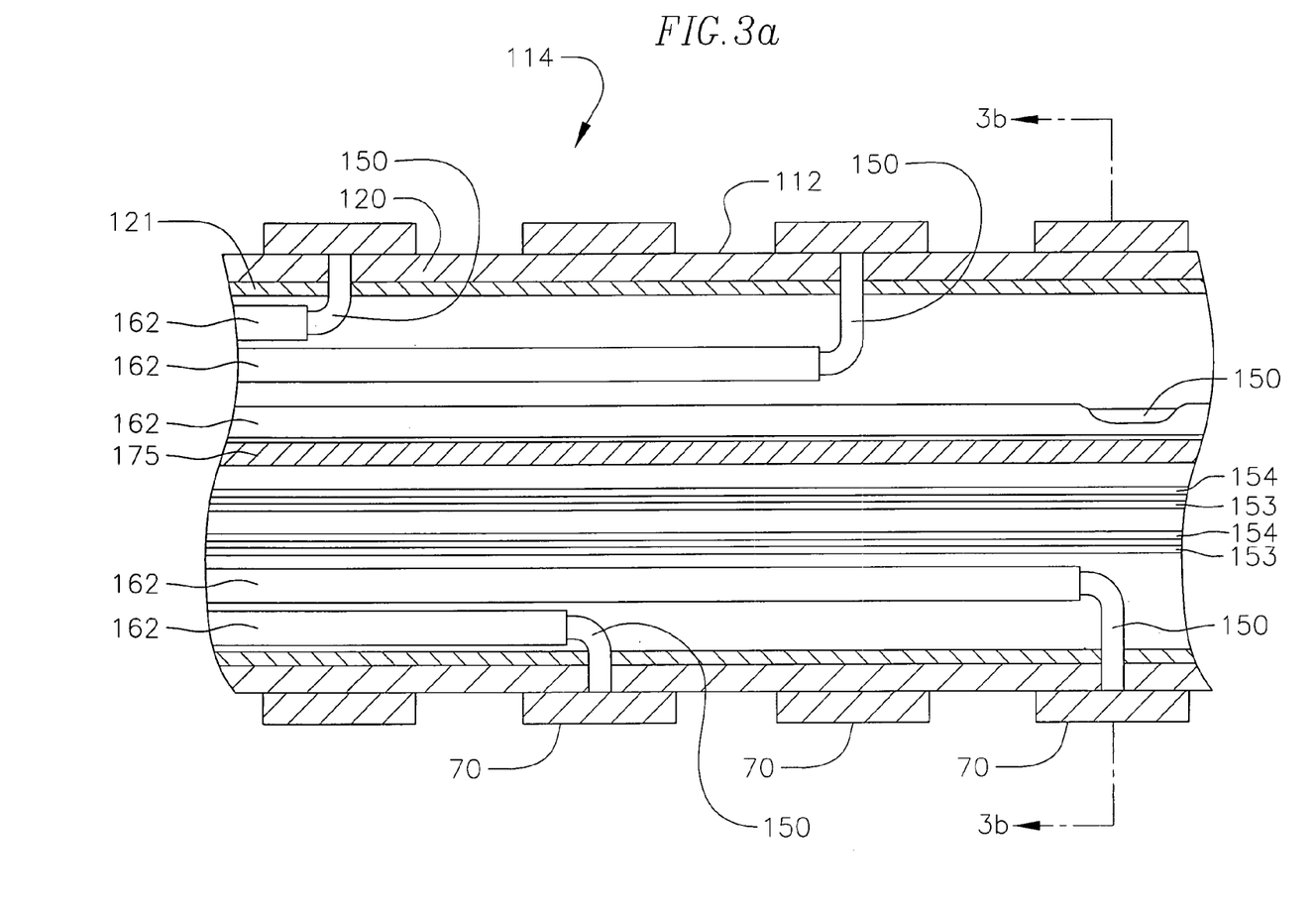
FIG. 3a is a side cross-sectional view of the proximal end of the catheter body of an esophagus probe catheter according to one embodiment of the present invention.
Figure 3B:
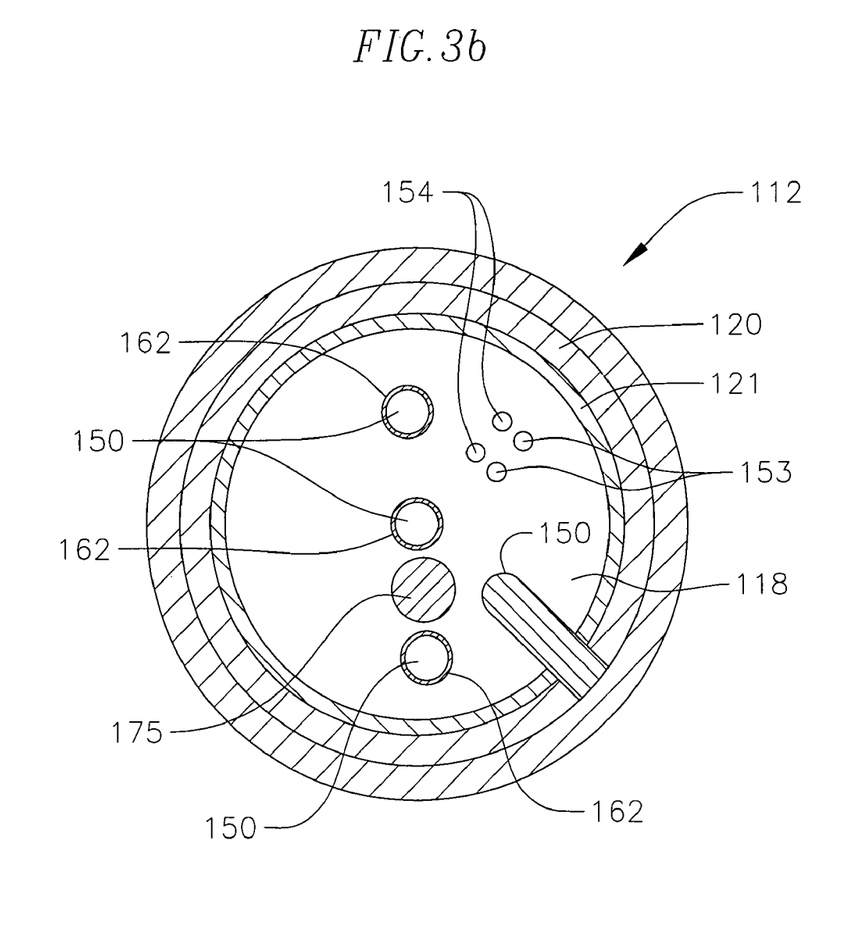
FIG. 3b is a longitudinal cross-sectional view of the proximal end of the catheter body of the esophagus catheter of FIG. 3a, taken along line 3b-3b.
Figure 3C:
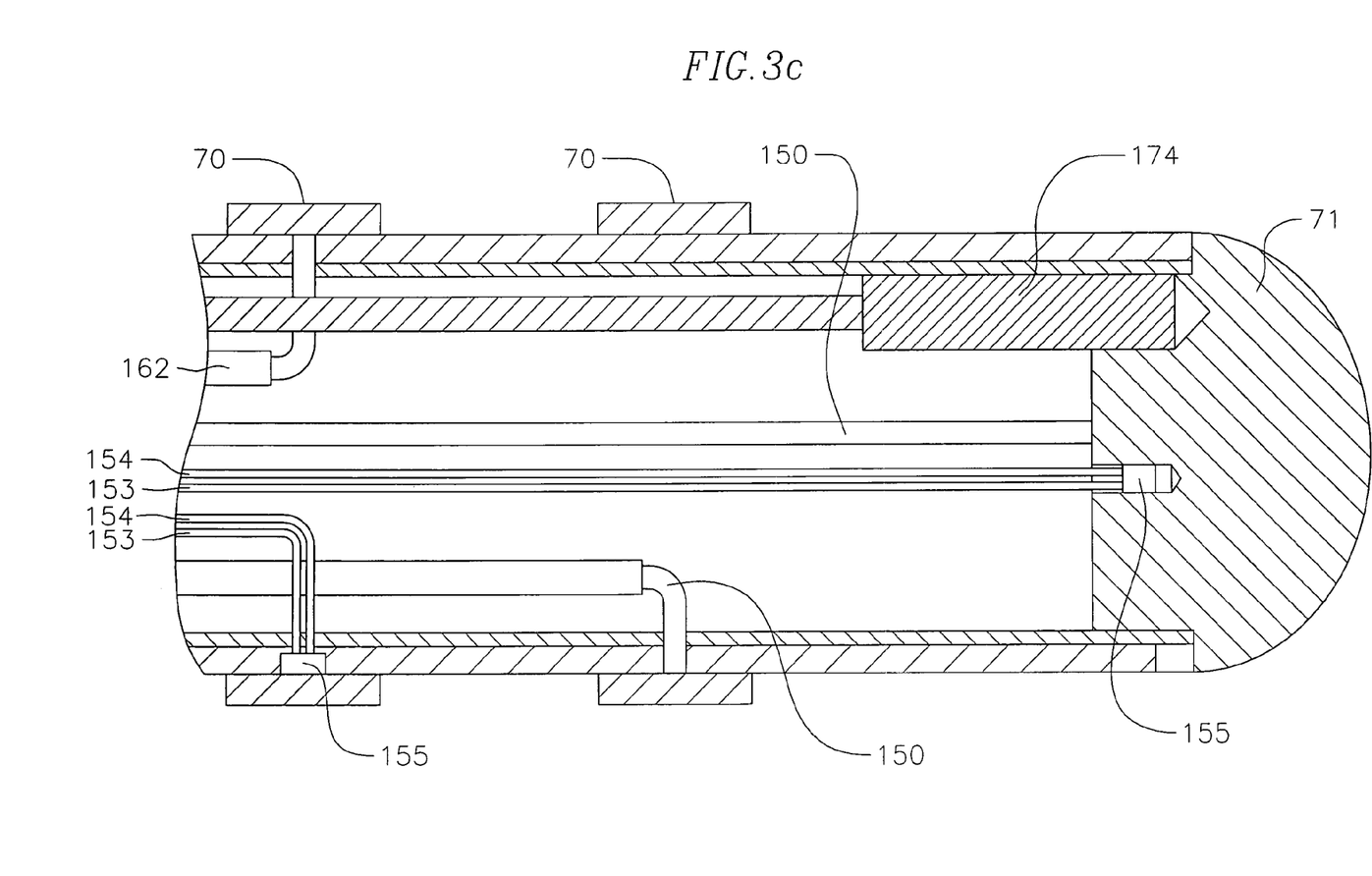

With reference to FIG. 3, the catheter body 112 comprises an elongated tubular construction having a single, axial or central lumen 118. The catheter body 112 is flexible, i.e., bendable, but substantially non-compressible along its length. The catheter body 112 can be of any suitable construction and made of any suitable material. One exemplary construction comprises an outer wall 120 made of polyurethane or PEBAX. The outer wall 120 may also be made of a suitable silicone containing material. The outer wall 120 comprises an embedded braided mesh of stainless steel or the like to increase torsional stiffness of the catheter body 112 so that, when the proximal portion of the body 112 is rotated, portion of the catheter body 12 distal thereto will rotate in a corresponding manner.

The outer diameter of the catheter body 112 is not critical, but is preferably no more than about 8 french, more preferably about 7 french. Likewise, the thickness of the outer wall 120 is not critical, but is thin enough so that the central lumen 118 can accommodate one or more lead wires and any other desired wires, cables or tubes. If desired, the inner surface of the outer wall 120 is lined with a stiffening tube 121 to provide improved torsional stability. In on embodiment, the outer wall 120 with an outer diameter of from about 0.090 inches to about 0.094 inches and an inner diameter of from about 0.061 inches to about 0.065 inches.

The catheter body 112, i.e., that portion that can be inserted into the patient, can vary as desired. Preferably, the length ranges from about 110 cm to about 120 cm. The distal region 114 on which the electrodes 71 and 70 are mounted ranges in length from about 1 cm to 8 cm, or about 2 cm to 7 cm or about 3 cm to 6 cm.

The tip electrode 71 is mounted on the distal end of the catheter body 112. The ring electrodes 70 are preferably spaced apart from each other such that the electrodes span substantially the entire length of the distal region 114 of the catheter body 112. A plurality of mapping electrodes is preferred in most instances in order to ensure accurate determination of the location of the catheter EC relative to the heart catheter HC. The ring electrodes and/or the tip electrode may be formed, at least in part, of a radiopaque material to aid in the alignment, under fluoroscopy, of the electrodes along the posterior wall of the left atrium.

Each ring electrode 70 and the tip electrode 71 is connected to a corresponding lead wire 150. The distal end of each lead wire 150 is attached to the corresponding electrode. The proximal end of each lead wire 150 is electrically connected to the SPU 34, where the electrical signals received from the electrodes are analyzed with reference to the electrical proximity signals generated by the signal generator 80 to determine the proximity between the catheters as a means to monitor the distance between the distal tip of the heart catheter HC and the superior wall 13 of the esophagus. As understood by one of ordinary skill in the art, the electrodes of the esophagus catheter may receive or transmit proximity signals, and the electrodes of the heart catheter may correspondingly transmit or receive proximity signals.

As shown in FIG. 3, the lead wires 150 are enclosed within a protective sheath 162 to prevent contact with other components within the lumen of the catheter body 112. The protective sheath 162 can be made of any suitable material, preferably polyimide. The protective sheath 162 is anchored at its distal end to the proximal end of the catheter body 112 by gluing it to the side wall of the catheter body 112 with polyurethane glue or the like. As would be recognized by one of ordinary skill in the art, the protective sheath 162 can be eliminated if desired.

One or more temperature sensors may be provided in the distal region 114 of the catheter body 112 to monitor the temperature of the esophageal tissue. Monitoring the temperature of the esophageal tissue allows the physician to control power delivery during ablation with the heart catheter HC in order to prevent thermal damage to the esophagus.

Any conventional temperature sensors, e.g. thermocouples or thermistors, may be used. In the embodiment shown in FIGS. 3a and 3c, the temperature sensors comprise thermocouples formed by enameled wire pairs. One wire of each wire pair is a copper wire 153, e.g., a number 40 copper wire. The other wire of each wire pair is a constantan wire 154. The wires 153 and 154 of each wire pair are electrically isolated from each other except at their distal ends where they are twisted together, covered with a short piece of plastic tubing 155, e.g., polyimide, and covered with epoxy. The plastic tubings 155 are anchored to the side wall of the catheter body 112 by glue or the like. The temperature sensors may be anchored anywhere along the length of the catheter body 112, such that the temperature of the esophageal tissue can be monitored. The wires 153 and 154 extend through the central lumen 118 of the catheter body and out to a connector (not shown) connectable to a temperature monitor (not shown). As noted above with respect to the lead wires 150, the wires 153 and 154 may be encased within a protective sheath 162, which can be made of any suitable material, preferably polyimide. The protective sheath 162 is anchored at its distal end to the side wall of the catheter body 112 by gluing it to the side wall with polyurethane glue or the like.

An electromagnetic sensor 174 may be contained within the distal end of the esophagus catheter EC. The electromagnetic sensor 174 is mounted to the side wall of the catheter body 112 by any suitable means, e.g., by polyurethane glue or the like. The electromagnetic sensor 174 may be used to ensure that the distal end of the catheter EC is positioned in the esophagus at a location below the left atrium of the heart. Positioning the tip of the catheter EC generally below the left atrium ensures that the plurality of ring electrodes 70 on the distal region 114 are aligned along the posterior wall of the left atrium, and that the electrodes 70 and 71 span substantially the length of the posterior left atrial wall. The electromagnetic sensor 174 may also be used to determine the proximity of the esophagus to the heart catheter HC, as discussed further below.

The electromagnetic sensor 174 is connected to an electromagnetic sensor cable 175, which extends through the central lumen 118 of the catheter body 112, and out through the electrical connector 37. The electromagnetic sensor cable 175 comprises multiple wires encased within a plastic covered sheath. The PIU 24 amplifies the signal received from the electromagnetic sensor 174 and transmits it to the COM unit 20. Because the catheter EC is designed for a single use only, the circuit board may contain and EPROM chip which shuts down the circuit board approximately 24 hours after the catheter has been used. This prevents the catheter, or at least the electromagnetic sensor from being used twice. Suitable electromagnetic sensors for use with the present invention are described, for example, in U.S. Pat. Nos. 5,558,091, 5,443,489, 5,480,422, 5,546,951 and 5,391,199, the entire disclosures of which are incorporated herein by reference.

As discussed above, the SPU 34 analyzes the electrical signals received from the electrodes of the esophagus catheter EC and the heart catheter HC. Once analyzed, the SPU 34 generates a signal to alert the physician to the proximity of the esophagus to the distal tip region of the heart catheter HC. In one embodiment, the SPU 34 analyzes the signals through impedance measurement. Using this technique, the impedance between the electrodes on the esophagus catheter and those on the heart catheter is continuously measured. A decrease in impedance between the two catheters indicates that the electrode(s) on the heart catheter is close to the esophagus. In one embodiment, when the impedance measurement drops below a predetermined threshold value, the physician is alerted that the electrode(s) of the heart catheter is too close to the esophagus.

In an alternative embodiment, pacing signal amplitude measurement is used to measure the proximity of the ablation electrode(s) to the esophagus. Using this technique, a pacing signal is sent to the electrodes on the esophagus probe catheter EC and is detected by the electrode(s) on the heart catheter HC. As the two catheters come into proximity of each other, the amplitude of the pacing signal increases, indicating that the electrode(s) of the heart catheter HC are close to the esophagus. When the amplitude of the pacing signal rises above a threshold value, the physician is alerted that the electrode(s) of the heart catheter HC are too close to the esophagus.

In yet another embodiment, a magnetic field may be used to determine the proximity of the ablation electrode(s) to the esophagus. Using this technique, both the catheters EC and HC comprise electromagnetic sensors. With the magnetic fields generated by the location pad 22, the electromagnetic sensors of the catheters generate electrical signals indicative of their location within the magnetic fields. This locational information enables the physician to determine the proximity of the ablation electrode(s) to the esophagus. Other suitable techniques for determining the proximity of the ablation electrode to the esophagus include inductance measurement, capacitance measurement and the use of Hall effect sensors.

In use, the esophagus catheter EC is inserted into the esophagus of a patient. The esophagus catheter may guided into the esophagus under fluoroscopy to align the electrodes along the posterior left atrial wall 14. The esophagus catheter EC remains in the esophagus for the duration of the catheter-based endocardial procedure. Before or after placement of the esophagus catheter EC, the heart catheter HC is inserted into the left atrium of the patient's heart, and tissue in the left atrium is mapped and/or ablated using the at least one electrode of the heart catheter. During the endocardial procedure, at least one electrode of one catheter transmits a proximity signal to at least one electrode of the other catheter. The SPU 34 compares the signals at the electrodes of the two catheters to determine the proximity of the catheters and generates a signal to inform, if not alert, the physician of the proximity. The system monitors the proximity on a continuous, real-time basis during the endocardial procedure.

The preceding description has been presented with reference to presently preferred embodiments of the invention. Workers skilled in the art and technology to which this invention pertains will appreciate that alterations and changes to the described structure may be practiced without meaningfully departing from the principal, spirit and scope of this invention. Accordingly, the foregoing description should not be read as pertaining only to the precise structures described and illustrated in the accompanying drawings, but rather should be read consistent with and as support for the following claims which are to have their fullest and fairest scope.

What is claimed is:

1. A system for monitoring proximity between a cardiac catheter and an esophagus of a patient, the system comprising:
    a cardiac catheter positioned in a heart of the patient;
    an esophagus catheter positioned to remain in the esophagus of the patient, wherein the esophagus catheter comprises a closed distal end;
    a proximity signal transmitted between the cardiac catheter and the esophagus catheter;
    a signal processing unit in electrical communication with the cardiac catheter and the esophagus catheter;
    wherein the catheters are separated by a distance from each other and the signal processing unit processes the proximity signal transmitted by one of the catheters and received by the other of the catheters to measure in real-time a characteristic of the signal for determining the distance between the catheters,
    wherein the system is configured to trigger an audio and/or visual signal to a user when a pre-determined distance between the catheters is reached.

2. A system of claim 1, wherein the characteristic is impedance.

3. A system of claim 1, wherein the characteristic is amplitude.

4. A system of claim 1, wherein the characteristic is phase.

5. A system of claim 1, wherein the proximity signal is transmitted from the cardiac catheter to the esophagus catheter.

6. A system of claim 1, wherein the proximity signal is transmitted from the esophagus catheter to the cardiac catheter.

7. A system of claim , wherein the proximity signal is a pacing signal.

8. A system of claim 1, wherein the signal processing unit processes the proximity signal in real time.

9. A system of claim 1, wherein the cardiac catheter is positioned in a left atrium of the heart.

10. A system of claim 1, wherein the cardiac catheter is adapted for mapping.

11. A system of claim 1, wherein the cardiac catheter is adapted for ablation.

12. A system of claim 1, wherein the esophagus catheter comprises:
    an elongated catheter body having at least one lumen therethrough; and
    at least one electrode mounted on the elongated catheter body.

13. A system of claim 1, wherein the cardiac catheter comprises an electrode and the esophagus catheter comprises an electrode and the distance extends between said electrodes.

14. A system of claim 1, wherein the signal processing unit continuously processes the proximity signal transmitted by one of the catheters and received by the other of the catheters.

15. A system for measuring proximity between a cardiac catheter and an esophagus of a patient, the system comprising:
- a cardiac catheter positioned in a heart of the patient, the cardiac catheter having a location sensor for detecting location signals;
- a first processor adapted to process the location signals to determine location of the cardiac catheter in the patient's heart;
- an esophagus catheter positioned to remain in the esophagus of the patient and positioned a distance from the cardiac catheter, wherein the esophagus catheter comprises a closed distal end;
- a proximity signal transmitted between the cardiac catheter and the esophagus catheter;
- a second processor adapted to process the proximity signal transmitted by one of the catheters and received by the other of the catheters to measure in real-time the distance between the catheters,
- wherein the system is configured to trigger an audio and/or visual signal to a user when a pre-determined distance between the catheters is reached.

16. A system of claim 15, wherein the second processor measures impedance of the proximity signal.

17. A system of claim 15, wherein the second processor measures amplitude of the proximity signal.

18. A system of claim 15, wherein the second processor processes the proximity signal on a real-time basis.

\* \* \* \* \*